United States Patent [19]

Miller

[11] Patent Number: 5,420,110
[45] Date of Patent: May 30, 1995

[54] COMPOSITIONS AND METHODS FOR INHIBITING ELASTASE

[75] Inventor: Edward J. Miller, Birmingham, Ala.

[73] Assignee: UAB Research Foundation, Birmingham, Ala.

[21] Appl. No.: 919,992

[22] Filed: Jul. 27, 1992

Related U.S. Application Data

[63] Continuation of Ser. No. 687,372, Apr. 18, 1991, abandoned.

[51] Int. Cl.$^6$ .................... A61K 38/43; A61K 38/55
[52] U.S. Cl. ........................ 514/12; 530/324; 435/218
[58] Field of Search .............. 435/218; 530/324; 514/12

[56] References Cited

U.S. PATENT DOCUMENTS

| | | | |
|---|---|---|---|
| 4,485,100 | 1/1984 | Hochstrasser et al. | 530/324 |
| 4,496,689 | 1/1985 | Mitra | 525/54.1 |

FOREIGN PATENT DOCUMENTS 630151 10/1961 Canada ........................ 435/218

OTHER PUBLICATIONS

Satoh et al, The Dual Nature of the Reaction Between Porciene Elastase and Human Plasma a, Prdenare Inhibitor vol. 86, No. 1, 1979. Biochem Biophys Res.

Lo et al. The Interaction of α-1-Antitrupsin with Soluble and Sepharnose Sound Elastase. Biochem & Biophys Acta 453 (1976), 344–346.

Perlmutter, et al., "Identification of a serpin-enzyme complex receptor on human hepatoma cells and human monocytes," *Proc. Natl. Acad. Sci. USA* 87:3753-3757 (1990).

Kress et al., "Characterization of the Inactive Fragment Resulting from Limited Proteolysis of Human $\alpha_1$-Proteinase Inhibitor by Crotalus adamanteus Proteinase II", *The Journal of Biological Chemistry*, 254:5317-53200 (1979).

Michaelis, et al., "Human neutrophil collagenase cleaves $\alpha_1$-antitrypsin", *Biochem. J.* 270:809-814 (1990).

Carrell et al., "Serpins: the superfamily of plasma serine proteinase inhibitors," in *Proteinase Inhibitors* (Barrett and Salvesen, eds.), Chapter 12, pp. 403-420.

Primary Examiner—Howard E. Schain
Assistant Examiner—L. Touzeau
Attorney, Agent, or Firm—Needle & Rosenberg

[57] ABSTRACT

This invention provides a compound comprising:
(1) a polypeptide moiety having
  a) an identifying number of amino acids for SPAAT,
  b) an elastase binding activity; and
(2) an extracellular matrix protein bound to the polypeptide moiety.

Also provided is a method of inhibiting an elastase comprising contacting the elastase with a polypeptide moiety having:
(1) an identifying number of amino acids for SPAAT;
(2) a collagen binding activity; and
(3) elastase binding activity.

8 Claims, 3 Drawing Sheets

```
                    V       IV      III              II      I
RESIDUE #   350 ↓        ↓       ↓                ↓       ↓     360

AAT:     ALA - MET - PHE - LEU - GLU - ALA - ILE - PRO - MET - SER - ILE -

SPAAT:         MET - PHE - LEU - GLU - ALA - ILE - PRO - MET - SER - ILE -

370
AAT:           PRO - PRO - GLU - VAL - LYS - PHE - ASN - LYS - PRO - PHE -

SPAAT:         PRO - PRO - GLU - VAL - LYS - PHE - ASN - LYS - PRO - PHE -

380
AAT:           VAL - PHE - LEU - MET - ILE - GLU - GLN - ASN - THR - LYS -

SPAAT:         VAL - PHE - LEU - MET - ILE - GLU - GLN - ASN -(THR)- LYS -

390
AAT:           SER - PRO - LEU - PHE - MET - GLY - LYS - VAL - VAL - ASN -

SPAAT:         SER - PRO - LEU - PHE - MET - LEU - LYS - VAL - VAL - SER -

394
AAT:           PRO - THR - GLN - LYS - COOH

SPAAT:
```

FIG.1

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Ala  Met  Phe  Leu  Glu  Ala  Ile  Pro  Met  Ser  Ile  Pro  Pro  Glu  Val  Lys
 1              5                        10                       15

Phe  Asn  Lys  Pro  Phe  Val  Phe  Leu  Met  Ile  Glu  Gln  Asn  Thr  Lys  Ser
               20                       25                       30

Pro  Leu  Phe  Met  Gly  Lys  Val  Val  Asn  Pro  Thr  Gln  Lys
               35                       40                       45
```

( 2 ) INFORMATION FOR SEQ ID NO:2:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met  Phe  Leu  Glu  Ala  Ile  Pro  Met  Ser  Ile  Pro  Pro  Glu  Val  Lys  Phe
 1              5                        10                       15
```

```
              Asn  Lys  Pro  Phe  Val  Phe  Leu  Met  Ile  Glu  Gln  Asn  Thr  Lys  Ser  Pro
                             20                      25                      30

Leu  Phe  Met  Leu  Lys  Val  Val  Ser
                             35                 40
```

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
              Met  Phe  Leu  Glu  Ala  Ile  Pro  Met  Ser  Ile  Pro  Pro  Gln  Val  Lys  Phe
              1                   5                      10                      15

Asn
```

( 2 ) INFORMATION FOR SEQ ID NO:4:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
              Met  Phe  Leu  Glu  Ala  Ile  Pro  Met  Ser  Ile  Pro  Pro  Glu  Val  Lys  Phe
              1                   5                      10                      15

Asn  Lys  Pro  Phe  Val  Phe  Leu  Met  Ile  Glu  Gln  Asn  Thr  Lys  Ser  Pro
                             20                      25                      30

Leu  Phe  Met  Gly  Lys  Val  Val  Asn  Pro  Thr  Gln  Lys
                             35                 40
```

COMPOSITIONS AND METHODS FOR INHIBITING ELASTASE

This invention was made with government support under Grant Number DE-08520 from the National Institutes of Health, U.S. Public Health Service. The United States government has rights in the invention.

This application is a continuation of application Ser. No. 07/687,372, filed Apr. 18, 1991, abandoned.

Throughout this application various publications are referenced. The citations are provided immediately preceding the claims. The disclosures of these publications in their entireties are hereby incorporated by reference into this application in order to more fully describe the state of the art to which this invention pertains.

BACKGROUND OF THE INVENTION

α1 Antitrypsin (AAT) is a 52 kDa plasma serine protease inhibitor. Its normal plasma concentration ranges from 150 to 350 mg/d1 (Brantly et al., 1988), although it behaves as an acute phase reactant increasing 3–4-fold during host response to inflammation and/or tissue injury such as with pregnancy, acute infection, tumors, estrogen, and typhoid vaccine (Kushner, 1988; Schreiber, 1987). AAT is capable of inhibiting a variety of proteases including trypsin, chymotrypsin, plasmin, thrombin, kallikrein, factor Xa, plasmogen and cathepsin G (Carrel et al., 1986; Laurell & Jeppson 1975; Travis & Salvesen, 1983), but its main physiological role is the inhibition of neutrophil elastase. Neutrophil elastase is not only capable of attacking elastin but may also cleave other connective tissue proteins, such as type I, III, and IV collagens, the protein portion of proteoglycans, and laminin (Bieth, 1986). AAT, however, prevents such degradation by forming a tightly bound 1:1 enzyme:inhibitor complex resulting in the slow proteolytic cleavage of the reactive center of the inhibitor between MET-358 and SER-359 of AAT (see SEQ ID NO:1).

The reactive center of human AAT (see SEQ ID NO: 1) is contained within an exposed peptide from (ALA-350) to (SER-359) in a stressed loop configuration (Carrell, 1986; Bruch et al., 1988), which may be comparable to the bait region of α-2-macroglobulin (S-Jensen, 1987). Every serine proteinase so far examined, including bacterial, plant, and reptilian as well as mammalian enzymes, has been reported to disrupt bonds within this loop of the native inhibitor. Cathepsin L (Johnson et al., 1986) and *Serratia marcescens* metalloproteinase (Virca et al., 1982), for example, have been reported to cleave the peptide bond between MET-358 and SER-359, while *Pseudomonas aeruginosa* (Morihara et al., 1984), macrophage elastase (Banda et al., 1985) and PNM collagenase (Knäuper et al., 1990) have been reported to cleave one amino acid residue N-terminal at the peptide bond between PRO-357 and MET-358. Cathepsin L (Johnson et al., 1986) and *Staphylococcus aureus* cysteine and serine proteinase (Potempa et al., 1986) have also been reported to cleave the peptide bond between GLU-354 and ALA-355, while *Staphylococcus aureus* metalloproteinase (Potempa et al., 1986), secreted PMN metalloproteinase (Desochers and Weiss, 1988, Vissers et al., 1988), and PMN collagenase (Knäuper et al., 1990) have been reported to cleave two amino acids N-terminal at the peptide bond between PHE-352 and LEU-353. In addition, *Crotialus adamenteus* (The Eastern Diamondback Rattlesnake) venom proteinase II has been reported to cleave the peptide bond between ALA-350 and MET-351. While cleavage of the inhibitor does not effect the inhibition of the bound AAT, the general consensus is that such fluid-phase cleavage inactivates the inhibitor from inhibiting other proteases. (Michaelis et al., 1990; Knäuper et al., 1990). There currently is no known function of the smaller cleaved peptide, although it may bind hepatoma and monocyte receptors (Perimutter et al, 1990).

Kress et al., 1989, report that venom proteinase II from the Eastern Diamondback Rattlesnake cleaves AAT in-vitro between ALA-350 and MET-351 (see SEQ. ID NO:1). Additionally, Kress et al., disclosed that ,one of the fragments produced in the cleavage has the NH₂ terminal sequence: Met-Phe-Leu-Glu-Ala-Ile-Pro-Met-Ser-Ile-Pro-Pro-Gln-Val-Lys-Phe-Asn (SEQ ID NO:3). Kress et al., disclose no activity for the fragment and disclose that the fragment does not inhibit the cleavage of trypsin by an elastase.

This invention provides the discovery that a 44-residue, C-terminal fragment of AAT (see SEQ ID NO:1) (hereinafter designated "SPAAT"(SEQ ID NO:4)) exists in human subjects. This fragment appears to represent the same fragment disclosed by Kress et al. when AAT was cleaved by snake venom proteinase II. However, despite the absence of activity being attributed to any small fragment of cleaved AAT in the literature and the finding in Kress et al. of no activity associated with the fragment, this invention provides the surprising discovery that SPAAT (SEQ ID NO:4) is in fact a potent inhibitor of elastase. Additionally, the invention provides the completely unexpected discovery that SPAAT (SEQ ID NO:4), when bound by an extracellular matrix protein such as a collagen, inhibits elastase to a much greater degree than SPAAT (SEQ ID NO. 4) alone.

Since SPAAT (SEQ ID NO:4), or equivalent polypeptides can be synthesized, the invention provides a much needed effective and inexpensive method to treat conditions such as emphysema and respiratory distress syndrome. Additionally, because of the discovery that the unique association of SPAAT (SEC ID NO:4) with the extracellular matrix (ECM) greatly increases the half-life, SPAAT (SEQ ID NO:4) can be administered much less frequently than AAT. This leads to less expensive administration and greater quality of life for the patient.

Finally, since the invention demonstrates that in vivo SPAAT (SEQ ID NO:4) is bound or deposited on biologically susceptible ECM proteins, such as elastin or collagen, SPAAT (SEQ ID NO:4) can be used in protectng these proteins from the inappropriate attack of enzymes like HNE.

SUMMARY OF THE INVENTION

This invention provides a compound comprising:
(1) a polypeptide moiety having
   a) an identifying number of amino acids for SPAAT (SEQ ID NO:4),
   b) an elastase binding activity; and
(2) an extracellular matrix protein bound to the polypeptide moiety.

Also provided is a method of inhibiting an elastase comprising contacting the elastase with a polypeptide moiety having:
(1) an identifying number of amino acids for SPAAT (SEQ ID NO:4) ;
(2) a collagen binding activity; and (3) elastase binding activity.

BRIEF DESCRIPTION OF THE FIGURES

FIG. 1 shows a comparison of C-terminal amino acid sequence of AAT (SEQ ID NO:1) with that of the sequenced portion of SPAAT (SEQ ID NO:2) isolated from human placenta. Residue numbering represents the position of each amino acid within the intact AAT sequence. The two differing residues, LEU-386 and SER-390, are underlined. Arrows (↓) indicate the cleavage sites of various proteolytic enzymes on complexing with AAT: I=Cathepsin L, *Serretta marcescens* matalloproteinase. II=*Pseudomonas aeruginosa*, macrophage elastase, PMN collagenase. III=Cathepsin L, *Staphylococcus aureus* cysteine and serine proteinase. IV=*Staphylococcus aureus* metalloproteinase, secreted PMN metalloproteinase, PMN collagenase. V=*Crotialus adamanteus* venom proteinase II.

DETAILED DESCRIPTION OF THE INVENTION

Figure 2:
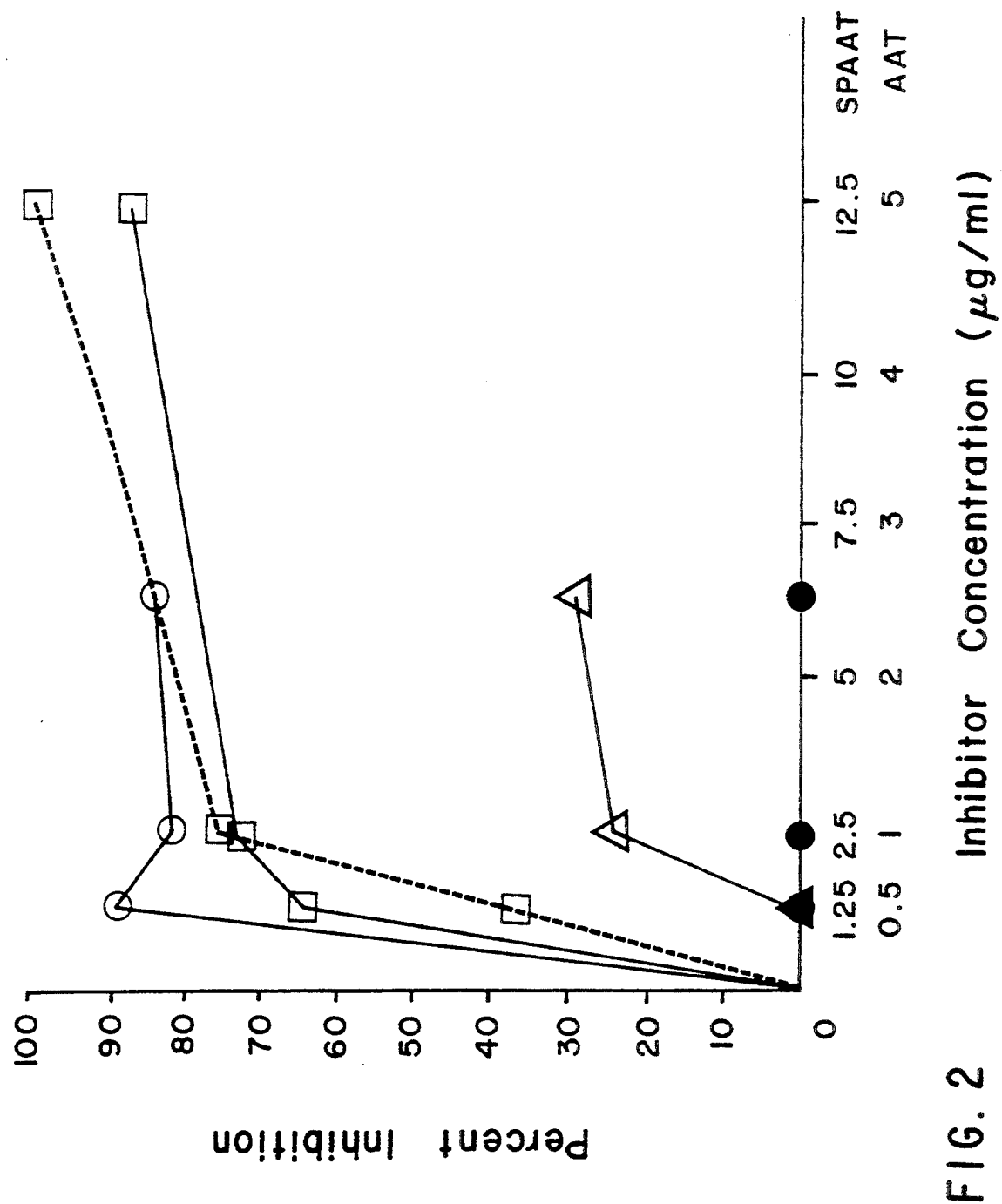
FIG. 2 shows the inhibition of various serine proteases by SPAAT (SEQ ID NO:4). Chymotrypsin (O); HNE (square); Pancreatic elastase (triangle); Trypsin (.). For comparison, the inhibition of HNE by AAT ( - - - ) under these assay conditions was also determined.

The data presented below demonstrates that the C-terminal 44 amino acid reactive center containing fragment of AAT (SEQ ID NO:1), SPAAT (SEQ ID NO:4), can be tissue bound and play an important physiological role in the protection of ECM proteins from the inappropriate attack of HNE. SPAAT (SEQ ID NO:4) was isolated and sequenced (FIG. 1) from human placenta that had been extensively extracted. This binding, furthermore, appears to be specific as no human serum albumin (HSA), another plasma protein found in 10× the concentration of AAT, was detected by ELISA (Table I).

Thus, the invention provides a composition comprising:
(1) a polypeptide moiety having
   a) an identifying number of amino acids for SPAAT (SEQ ID NO:4) shown in FIG. 1,
   b) an elastase binding activity; and
(2) an extracellular matrix protein bound to the polypeptide moiety.

While FIG. 1 only discloses amino acids through position 390, the composition of this invention includes -PRO-THR-GLN-LYS, the amino acids at positions 391–394. Additionally, as noted elsewhere, positions 390 and 386 likely represent sequencing errors and should correspond to the sequence for AAT at those positions (see SEQ ID NO:1).

Given the sequence of SPAAT (SEQ ID NO:4), one could follow standard methods to make additions, substitutions and deletions to vary the sequence of SPAAT. These variations could be tested using the methods set forth in the example to determine elastase binding activity. Thus, "SPAAT" (SEQ ID NO:4) means a moiety which has the essential amino-acids of SPAAT (SEQ ID NO:4) for elastase and collagen binding activity.

As set forth in the examples, SPAAT (SEQ ID NO:4) binds an extracellular matrix protein Type I collagen to have an increased inhibitory capacity. Other extracellular matrix proteins would be expected to likewise increase activity by inducing a conformational change in the peptide. The reason for SPAAT's binding to collagen is likely due to hydrophobic interactions. SPAAT (SEQ ID NO:4) is a hydrophobic peptide and collagen has clusters of hydrophobic regions. Thus, since other extracellular matrix proteins likewise contain hydrophobic regions, especially elastin, they would be expected to have the same interactions. At any rate, such activity can be routinely tested based on the teaching in the example. Thus, only those extracellular matrix proteins which actually bind the polypeptide are included within the scope of the composition claim. Elastin is another example of an extracellular matrix protein which would be expected to bind the polypeptide moiety. Additionally, the compositions of the invention can be combined with a pharmaceutically acceptable carrier for administration.

The invention also provides a kit comprising:
(1) a polypeptide moiety having
   a) an identifying number of amino acids for SPAAT (SEQ ID NO:4),
   b) an elastase binding activity; and
(2) an extracellular matrix protein. The extracellular matrix protein can be a collagen, especially Type I collagen.

The invention still further provides a method of inhibiting an elastase comprising contacting the elastase with a polypeptide moiety having:
(1) an identifying number of amino acids for SPAAT (SEQ ID NO:4);
(2) a collagen binding activity; and
(3) elastase binding activity.

This method applies to any elastase which is bound by the moiety, for example neutrophil elastase. One would expect other elastases to be inhibited by the polypeptide moiety due to similarities of cleavage mechanisms and substrate specificities of the elastases. In one embodiment, the polypeptide moiety of the method has the identical amino acid sequence of SPAAT (SEQ ID NO:4).

Additionally, the method of inhibiting can be practiced by contacting the polypeptide moiety with an activity-enhancing extracellular matrix protein, for example, type I collagen or elastin, prior to contacting the elastase. Such a method can increase the activity of the polypeptide moiety leading to greater inhibitor activity.

Finally, the invention provides a method of treating an aberrant condition associated with proteolysis by neutrophil elastase in a subject comprising administering to the subject polypeptide moiety having:
(1) an identifying number of amino acids for SPAAT (SEQ ID NO:4);
(2) a collagen binding activity; and
(3) neutrophil elastase binding activity.

Many aberrant conditions can be treated by this method. The aberrant conditions include pulmonary emphysema and adult respiratory distress syndrome.

EXAMPLE

The following EXAMPLE, inter alia, describes the isolation of SPAAT (SEQ ID NO:4). It should be recognized that SPAAT (SEQ ID NO:4), given the sequence described herein, could be readily synthesized or recombinantly produced.

Methods

All compounds listed below are commonly used and available and any abbreviation utilized is readily known to the skilled artisan.

Isolation of SPAAT

All operations were performed at 4° C. and all extraction buffers contained 25 mM EDTA, 5mM benzamidine, 1 mM PMSF, 1 mMNEM to minimize protein degradation during processing. After removal of membranes, the human placenta tissue was minced with scalpels and washed extensively with 1M NaCl, 50 mM Tris, pH 7.5 to remove blood. The tissue was next extracted with several washes of 8M urea, 50 mM Tris, pH 7.8. The residue was then extracted with 2 volumes of 8M urea, 50 mM Tris, pH 7.8 containing 1% 2-ME. The supernatant was dialyzed extensively against 0.1M ammonium bicarbonate, 50 mM Tris, pH 8.0, centrifuged to remove insoluble material, and gently stirred overnight with DEAE Trisacryl which had been equilibrated in the same buffer. The DEAE was recovered by low speed centrifugation and washed for 10 min with an equal volume of bicarbonate buffer. After low speed centrifugation, the proteins of interest were eluted by stirring for 3 hrs in the same bicarbonate buffer containing 0.5M NaCl. The DEAE was removed by low speed centrifugation and the supernatant further clarified by ultracentrifugation. The solution was then dialyzed against distilled water and lyophilized to dryness. A 50 mg aliquot of the preparation was resuspended in 5 ml of 5.0M urea, 0.1M Tris, pH 8.5 containing 0.2M DTT for 5 hrs, then dialyzed against a large excess of 60 mM sodium acetate, pH 4.85. The material precipitating during dialysis was removed by centrifugation. This precipitate was similarly redissolved in the above urea-DTT solution and dialyzed versus the acetate buffer two additional times. The resultant pooled supernatants were subjected to ELISA and amino acid analysis to determine yield as well as amino acid sequence analysis.

ELISA

Plastic microtiter wells were coated overnight at 4° C. with 100 $\mu$ls of antigens appropriately diluted in PBS. Plates were washed 3× with approximately 300 $\mu$ls PBS/well. Any remaining reactive sites were blocked by adding 200 $\mu$ls 1% BSA in PBS/well and incubating for 1 hr at 37° C. The plates were again washed 3× with approximately 300 $\mu$ls PBS/well. The rabbit anti-human AAT and HSA polyclonal antibodies were diluted 1/40,000 with PBS containing 0.05% Tween-20. 50 $\mu$ls of this diluted primary antibody was added/appropriate well. The plate was again incubated for 1 hr at 37° C., then washed 3× with approximately 300 $\mu$ls PBS/well. 50 $\mu$ls of an appropriately diluted secondary antibody (goat anti-rabbit IgG diluted 1/16,000) was added/well. The plates were again incubated for 1 hr at 37° C., then washed 5× with approximately 300 $\mu$ls PBS/well. 50 $\mu$ls of color developing ortho-phenylenediamine (OPD) solution was added/well. The plates were incubated for 30 min at 37° C. The reaction was finally stopped by the addition of 50 $\mu$ls/well of 4.5M sulfuric acid and read at 492 nm.

An ELISA was also developed to quantitate the potential binding affinity of various antigens for AAT and/or SPAAT (SEQ ID NO:4). These ELISAs were done as outlined above, except (1) enzyme antigens (HNE, cathepsin G) were inactivated by DFP treatment prior to the ELISA to minimize potential artifacts due to the cleavage of detecting antibodies, (2) wells were coated with antigen solutions at approximately 40 $\mu$g/ml, and (3) after blocking wells were incubated with 10 $\mu$g/ml AAT or SPAAT (SEQ ID NO:4) in PBS for 2½ hrs at 37° C. Control wells were incubated with PBS alone. The binding of exogenous AAT and SPAAT (SEQ ID NO:4) to specific antigens was corrected for the non-specific binding of AAT and/or SPAAT (SEQ ID NO:4) to BSA.

Protein Sequencing

Edman degradations were performed in a Beckman Model 890M sequencer (Bhown & Bennett, 1985). Approximately 200 pmol of the peptide was used for sequencing. Two different placental SPAAT (SEQ ID NO:2) preparation were sequenced with identical results. Repetitive yields were generally between 96 and 99%. PTH amino acids were identified by HPLC as described by Bhown & Bennett (1985).

Enzyme Assays

Serine protease assays were performed using p-nitroanalide amide substrates. Trypsin activity was assayed by using Benzyl-PHE-VAL-ARG-PNA (0.5 mg/ml). Chymotrypsin activity was assayed by using SUC-(ALA)$_2$-PRO-PHE-PNA (10 mg/ml in DMSO). Elastase activity was assayed by using SUC-(ALA)$_3$-PNA (10 mg/ml in DMSO). The dilution of each of these enzymes required to produce a change in absorbance of approximately 0.4 after a 15 min incubation at 37° C. was initially determined. The complete reaction mixture contained 10 $\mu$ls of this enzyme dilution plus 100 $\mu$ls of the appropriate above substrate and 0-50 uls of the indicated concentration of inhibitor or TBS to maintain constant volume. Trypsin, chymotrypsin, and HNE assays were incubated at 37° C. for 15 min, while pancreatic elastase assays were incubated at 37° C. for 1.5 min. The reaction was terminated by the addition of a sufficient quantity of ice cold TBS to bring each assay up to a final volume of 1 ml. The absorbance of the p-nitroaniline produced was measured against a distilled water blank at 410 nm on a Hitachi model 100-40 spectrophotometer. Percent inhibition was calculated as: $100-[(A_1E+I/A_1E)\times 100]$.

Results

Extraction

As summarized in Table I for a typical preparation, milligram quantities of antigenically detectable AAT (or its cleavage fragment(s) including SPAAT (SEQ ID NO:4)) were recovered at each extraction step. In order to establish that the tissue binding of SPAAT (SEQ ID NO:4) was specific, we compared the amount of AAT reactivity in the extracts to that of another serum protein, HSA, which is found at 10 times the concentration of AAT in the plasma. As indicated in Table I, no HSA was detected in any of these fractions. Interestingly, even after this extensive extraction procedure some AAT antigenic activity remained associated with the acid insoluble precipitate. When this pellet was solubilized in 5.0M urea, 0.1M Tris, pH 8.5 containing 0.2M DTT and run on a molecular sieve column (Superose 6, Pharmacia), two peaks of AAT antigenic activity were recovered: a high molecular weight peak and a low molecular weight peak (data not shown) suggesting that some SPAAT (SEQ ID NO:4) might remain aggregated and/or be bound to one or more high molecular weight "carrier" protein(s).

Biochemical Characterization of SPAAT

When the DEAE-bound material was dissolved in 5M urea, 0.1M Tris, pH 8.5 containing 0.2M DTT and dialyzed against 60 mM sodium acetate buffer, pH 4.85, most of the protein appeared to be insoluble and precipitated. A small amount of protein (usually 10% or less) remained soluble. This supernatant was dialyzed, lyophilized, weighed, and resuspended in 50% acetic acid. An aliquot equivalent to approximately 200 pmoles was then subjected to amino acid sequence analysis. Its 40 residue N-terminal sequence is presented in FIG. 1. A computer comparison with the sequence of known proteins revealed that 38 of these 40 residues were identical to the C-terminal region of AAT (SEQ ID NO:1) beginning at MET-351, 7 amino acids N-terminal to the reactive center MET-358 (Long et al., 1984). The two differing residues, LEU-386 and SER-390, occurred near the C-terminus of the peptide when the sequence was becoming difficult to decipher and likely represent sequencing errors. Moreover, it is apparent that SPAAT (SEQ ID NO:4) is a 44 residue protein beginning at MET-351 and ending with LYS at 394 consistent with the COOH terminal sequence of AAT (SEQ ID NO:1).

Potential Physiological Significance

Inhibition of Enzyme Activity

Preliminary enzyme kinetic experiments presented in FIG. 2 indicate that our desalted SPAAT (SEQ ID NO:4) preparations preferentially inhibit chymotrypsin>HNE>pancreatic elastase, while having no effect on trypsin. Importantly, these SPAAT (SEQ ID NO:4) preparations inhibited HNE activity almost as well as native AAT. Preliminary calculations of the inhibitor concentrations required to totally inhibit chymotrypsin enzymatic activity indicate that SPAAT (SEQ ID NO:4) is a potent ($K_I \sim 1/10$ Km), competitive inhibitor of chymotrypsin.

Mode of Inhibition

Figure 3:
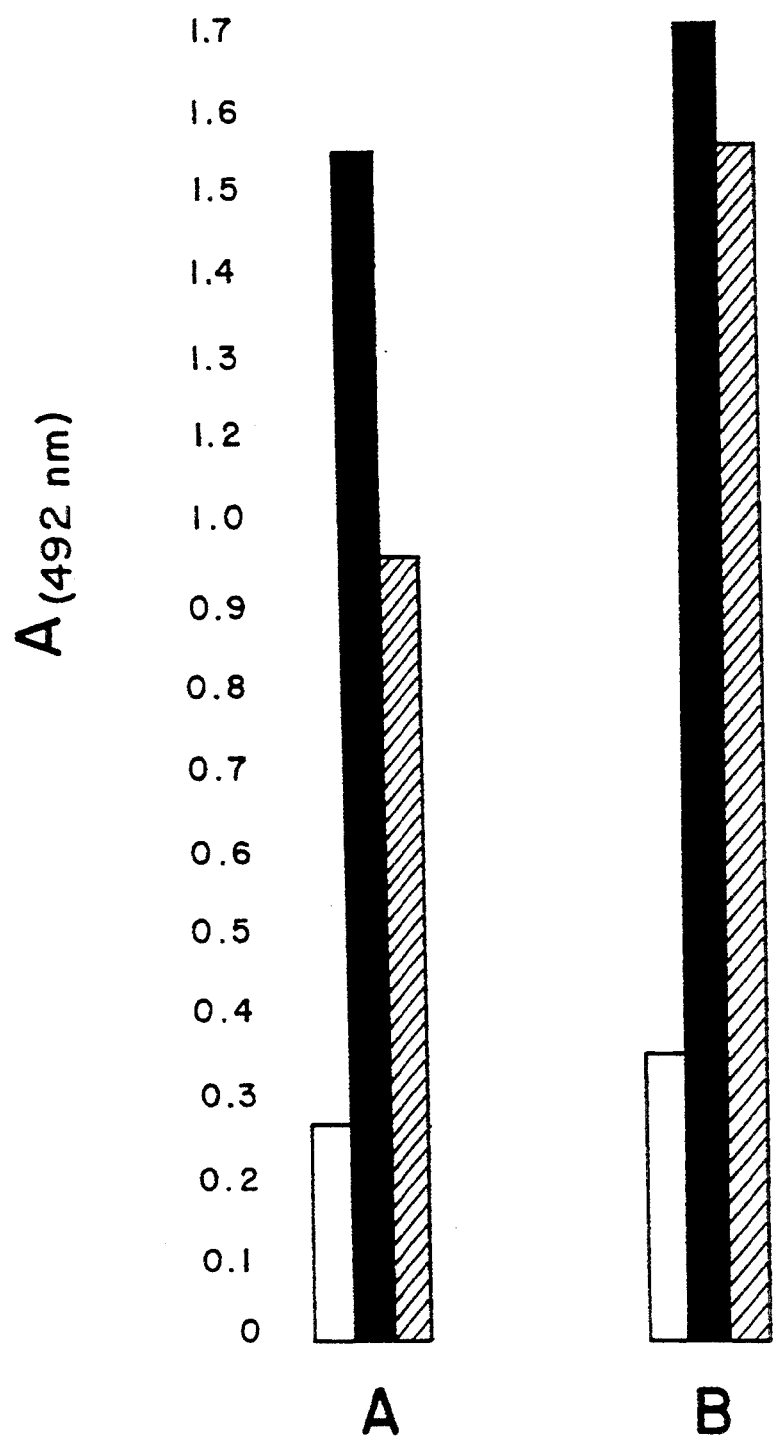
FIG. 3 shows the binding of AAT and SPAAT (SEQ ID NO:4) to DFP-treated human neutrophil: A. Elastase. B. Cathepsin G.

AAT inhibits serine protease activity by forming a covalent 1:1 enzyme:inhibitor complex involving its reactive center MET-358 (Johnson and Travis, 1978). If SPAAT (SEQ ID NO:4) acts similarly then it too should form such a stable enzyme:peptide complex. Thus, we tested the ability of SPAAT (SEQ ID NO:4) to bind to some physiologically relevant serine proteases and compared and contrasted this binding to that of AAT using our ELISA systems. As can be seen in FIG. 3, both AAT and SPAAT (SEQ ID NO:4) bound to DFP-treated HNE as well as cathepsin G.

BINDING COLLAGEN AND OTHER PROTEINS

Several additional observations indicate that SPAAT (SEQ ID NO:4) aggregates and/or binds to a larger molecular weight ECM "carrier" protein. First, immunohistochemical studies using antibidies against AAT reveal strong staining of the adventitia of vessels in placenta villi as well as around the alveoli and small bronchi of the lung. Secondly, SDS-PAGE of placental SPAAT (SEQ ID NO:4) preparations reveal several high molecular weight protein bands in addition to the lower molecular weight. SPAAT (SEQ ID NO:4) band. Moreover, amino acid analyis of our SPAAT (SEQ ID NO:4) preparations showed substantial amounts of hydroxyproline suggesting the presence of collagen chains with blocked N-termini since no collagen was detected in the sequencing studies. These results underscore the liklihood that in vivo SPAAT (SEQ ID NO:4) is bound to or deposited on biologically susceptible proteins and thus can play an important role in the protection of these proteins from inappropriate attack of serine proteases like HNE. Thus, SPAAT (SEQ ID NO:4) can be used in vivo to protect these proteins.

SPAAT BINDS AN EXTRACELLULAR MATRIX PROTEIN WHICH INCREASES ACTIVITY

In further inhibition studies using chymotrypsin as the subject enzyme, we noted that the $K_I(\mu M)$ for placental SPAAT (SEQ ID NO:4) is 0.92 while that for chemically synthesized SPAAT (SEQ ID NO:4) is 7.5. Thus, on a mole-for-mole basis, chemically synthesized SPAAT (SEQ ID NO:4) is an eight-fole less effective inhibitor of HNE than SPAAT (SEQ ID NO:4) isolated from placenta. These results demonstrate that association of the peptide with collagen in the placental material causes a conformational change more conducive to inhibitory capacity.

TABLE I
AMOUNT OF ELISA DETECTED PROTEIN AT VARIOUS STEPS IN THE SPAAT EXTRACTION

| Fraction | TOTAL DETECTED PROTEIN | |
|---|---|---|
| | AAT (mg) | HSA (mg) |
| 1. 8M urea (Third extract) | ≧22.14 | ND |
| 2. 8M urea + 2-ME (First extract) | ≧36.38 | ND |
| 3. 2M urea + 2-ME (Second extract) | ≧18.56 | ND |
| 4. Acid soluble supernatant | 0.337 | ND |
| 5. Acid insoluble precipitate (Resuspended in 250 uls PBS) | 0.0114 | ND |

AAT and HSA were detected antigenically by ELISA as described in the METHODS section of the test.
Experimental values were calculated from a standard curve using appropriate commercially available antigen. Some fractions (≧) probably represent a minimum estimate of protein as even the lowest dilutions tested still exhibited maximum antibody binding.
ND = none detected.

REFERENCES

1. Ashe, B. M. & Zimmerman, M. (1977). BBRC, 75, 194–199.
2. Bhown, A. S. & Bennett, J. C. (1985). Anal. Biochem., 150, 457–462.
3. Bieth, J. G. Elastases: Cathyltic and biological properties. In: Mecham R. ed. Regulation of matrix accumulation. New York: Academic Press, 1986; 217–320.
4. Brantly, M., Nukina, T., & Crystal, R. G. The Americal J. of Medicine, 84 (Suppl 6A) 13–31 (1988).
5. Bruch, M. Weiss, V., & Engel, J. (1988) J. Biol. Chem. 263, 16626–16630.
6. Carlson, J. A., B. Barton Rogers, R. N. Sifers, H.K. Hawkins, M. J. Finegold, & S. L. C. Woo, J. Clin. Invest., 82, 26–36 (1988).
7. Carrell, R. 1986 J. Clin. Invest., 78, 1427–1431.
8. Carrell, R. W. & Boswell D. R., Serpins. The superfamily of plasma serine proteinase inhibitors. In: Barrett A. J., Salvesen G., eds. Proteinase inhibitors. Amsterdam: Elsevier, 1986, 403–420.
9. Desroches, P. E. & Weiss, S.J. J. Clin. Invest., 81: 1646–1650 (1988).
10. Geboes, K. M. B. Ray, P. Rutgeerts, F. Callea, V. J. Desmet, & G. Vantrappen. 1982. Histopathology (Oxf.) 6: 55–60.

11. Huber, A. R. & Weiss, S. J., *J. Clin Invest.*, 83, 1122-1131 (1989).
12. Johnson, D. & Travis, J., *J. Biol. Chem.*, 253: 7142-7144 (1978).
13. Johnson, D., J. Barrett, & R. Mason. 1986 *J. Biol. Chem.*, 261, 14748-14751.
14. Kittas, C., K. Aroni, A. Matani, & C. S. Papadimitriou (1982). *Hepatogastroenterology*, 29: 275-277.
15. Knäuper, V., Reinke, H., & Tschesche, H. *FEBS Letters*, 263, 355-357 (1990).
16. Knudsen, B. S., R. L. Silverstein, L. L. K. Leung, P. C. Harpel, and R. L. Nachman. (1986) *J. Biol. Chem.*, 261: 10765-10771.
17. Kress, L. F., Kurecki, T., Char, S. K., Laskowski, M. Sr. (1979), *J. Biol. Chem.*, 254, 5317-5320.
18. Kushner, I. (1988) *Meth. Enzymol.*, 163, 373-383.
19. Laurell, C. B., & Jeppsson, J. O. (1975). Protease inhibitors in plasma. In "The Plasma Proteins" (F. W. Putnam, ed.), Vol 1, pp. 229-264, Academic Press, New York.
20. Long, G. L., Chandra, T., Woo, S. L. C., Davie, E. W., & Kurachi, K., *Biochemistry*, 23, 4828-4837 (1984).
21. Michaelis, J. M. C. M. Vissers, & C. C. Winterbourn, *Biochem J.* 270, 809-814 (1990).
22. Morihara, K. Tsuzuki, H., Harado, M., & Iwata, T. (1984) *J. Biochem.* 95, 795-804.
23. Nielsen, K. (1984) *Histopathology* (Oxf.) 8: 759-764.
24. Perlmutter, D. H., Glover, G. I., Rivetna, M. Schasteen, C. S., and Fallon, R. J., *Proc. Natl. Acad. Sci.*, 87, 3753-3752 (1990).
25. Potempa, J., Watorek, W., & Travis, J. *J. Biol. Chem.*, 261: 14330-14334, 1986.
26. Powers, J. C. & Harper, J.W. Inhibitors of serine proteinases. In: Barrett, A. J. & Salvesson, G., eds. Proteinases Inhibitors, Elsevier, N.Y. 1986 pgs 55-152.
27. Ray, M. B. V., V. J. Desmet, & W. Gepts, 1977 *Cell Tissue Res*, 185: 63-68.
28. Ray, M. B., K. Gebos, F. Callea, and V. J. Desmet (1982) *Histopathology* 6: 289-297.
29. Schreiber, G. (1987) in The Plasma Proteins (Putnam, F. W., ed) 2nd ed. Vol. 5, pp 292-363, Academic Press, New York.
30. Sinha, S. Watorek, W., Karr S., Giles, J. Bode, W. & Travis, J. (1987) *Proc Natl Acad Sci*, 84, 2228-2232.
31. S.-Jensen, L. (1987) in *The Plasma Proteins* (Putnam, F. W.; ed.) Vol 5, pp 191-291, Academic Press, New York. 32. Tahara, E., H. Ito, K. Taniyma, H. Yokozaki, & J. Hata (1984) *Hum. Pathol.* 15: 957-964.
33. Travis, J. & Salvesen G. S. Human plasma proteinase inhibitors. *Ann Rev Biochem* 1983; 52: 655-709.
34. Virca, G. D., Lyerly, D., Kreger A., & Travis J. (1982) *Biochem. Biophys. Acta*, 704, 267-271.
35. Wagner, D. D., M. Urban-Pickering, and V. J. Marden (1984) *Proc Natl Acad Sci*, 81: 471-475.
36. Banda, M., E. Clark & Z. Werb, 1985 *J. Clin. Invest.* 75, 1758-1762.

---

What is claimed is:

1. A method of inhibiting an elastase comprising contacting the elastase with a polypeptide moiety derived from the carboxyl terminal domain of alpha-1-antitrypsin having:
   a. the amino acid sequence for SPAAT (SEQ ID NO:4);
   b. a collagen binding activity; and
   c. elastase binding and inhibiting activity.

2. The method of claim 1, wherein the elastase is neutrophil elastase.

3. The method of claim 2, further comprising contacting the polypeptide moiety with an activity enhancing extracellular matrix protein prior to contacting the elastase.

4. The method of claim 3, wherein the extracellular matrix protein is a collagen.

5. The method of claim 4, wherein the collagen is type I collagen.

6. The method of claim 3, wherein the extracellular matrix protein is elastin.

7. A method of treating an aberrant condition, associated with proteolysis by neutrophil elastase in a subject comprising administering to the subject a polypeptide moiety derived from the carboxyl terminal domain of alpha-1-antitrypsin having:
   a. the amino acid for SPAAT (SEQ ID NO:4);
   b. a collagen binding activity; and
   c. neutrophil elastase binding and inhibiting activity.

8. The method of claim 7, wherein the aberrant condition is selected from the group consisting of pulmonary emphysema and adult respiratory distress syndrome.

* * * * *